(12) United States Patent
Eller

(10) Patent No.: US 9,347,533 B2
(45) Date of Patent: May 24, 2016

(54) ROTATIONAL DRIVE SYSTEM FOR A BIOPSY MEMBER

(71) Applicant: COOK MEDICAL TECHNOLOGIES LLC, Bloomington, IN (US)

(72) Inventor: Derek R. Eller, Orient, OH (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 328 days.

(21) Appl. No.: 13/948,560

(22) Filed: Jul. 23, 2013

(65) Prior Publication Data

US 2014/0026693 A1    Jan. 30, 2014

Related U.S. Application Data

(60) Provisional application No. 61/675,438, filed on Jul. 25, 2012.

(51) Int. Cl.
*A61B 10/02* (2006.01)
*F16H 19/04* (2006.01)

(52) U.S. Cl.
CPC .......... *F16H 19/043* (2013.01); *A61B 10/0233* (2013.01); *A61B 2010/0208* (2013.01); *Y10T 74/18096* (2015.01)

(58) Field of Classification Search
CPC .................... A61B 10/0233; F16H 19/043
See application file for complete search history.

(56) References Cited

U.S. PATENT DOCUMENTS

| 1,257,532 | A | 2/1918 | Risk |
| 1,708,888 | A | 4/1929 | Keeling |
| 1,833,344 | A | 11/1931 | West |
| 2,381,112 | A | 8/1945 | Clark |
| 2,710,000 | A | 6/1955 | Cromer et al. |
| 2,850,007 | A | 9/1958 | Lingley |
| 3,683,891 | A | 8/1972 | Eskridge et al. |
| 5,018,530 | A | 5/1991 | Rank et al. |
| 5,133,713 | A | 7/1992 | Huang et al. |
| 5,221,269 | A | 6/1993 | Miller et al. |
| 5,478,003 | A | * 12/1995 | Green et al. ............... 227/176.1 |
| 5,488,958 | A | 2/1996 | Topel et al. |
| 6,027,458 | A | 2/2000 | Janssens |
| 6,083,237 | A | 7/2000 | Huitema et al. |
| 6,530,936 | B1 | 3/2003 | Yun |
| 6,592,530 | B1 * | 7/2003 | Farhadi .............. A61B 10/0275 600/564 |
| 6,620,111 | B2 | 9/2003 | Stephens et al. |
| 6,860,860 | B2 | 3/2005 | Viola |
| 7,008,381 | B2 | 3/2006 | Janssens |
| 7,419,472 | B2 | 9/2008 | Hibner et al. |
| 7,662,109 | B2 | 2/2010 | Hibner |
| 7,670,328 | B2 | 3/2010 | Miller |
| 7,850,620 | B2 | 12/2010 | Miller et al. |
| 7,867,173 | B2 | 1/2011 | Hibner et al. |
| 2002/0138021 | A1 | 9/2002 | Pflueger |
| 2007/0191732 | A1 | 8/2007 | Voegele |
| 2009/0057369 | A1 * | 3/2009 | Smith et al. ................. 227/175.1 |
| 2010/0317995 | A1 | 12/2010 | Hibner et al. |
| 2012/0168485 | A1 * | 7/2012 | Marczyk et al. ........... 227/176.1 |

* cited by examiner

*Primary Examiner* — Sean Dougherty
(74) *Attorney, Agent, or Firm* — Brinks Gilson & Lione

(57) ABSTRACT

A drive system is provided for rotating a biopsy member. The drive system includes a pinion connected to the biopsy member and a rack that drives the pinion during a drive stroke. During the return stroke, the rack rotates away from the pinion so that the rack is not engaged with the pinion during the return stroke. Thus, the pinion is only driven during the drive stroke but not during the return stroke. As a result, the biopsy member rotates in a single direction as a trigger is repeatedly pressed and released.

20 Claims, 5 Drawing Sheets

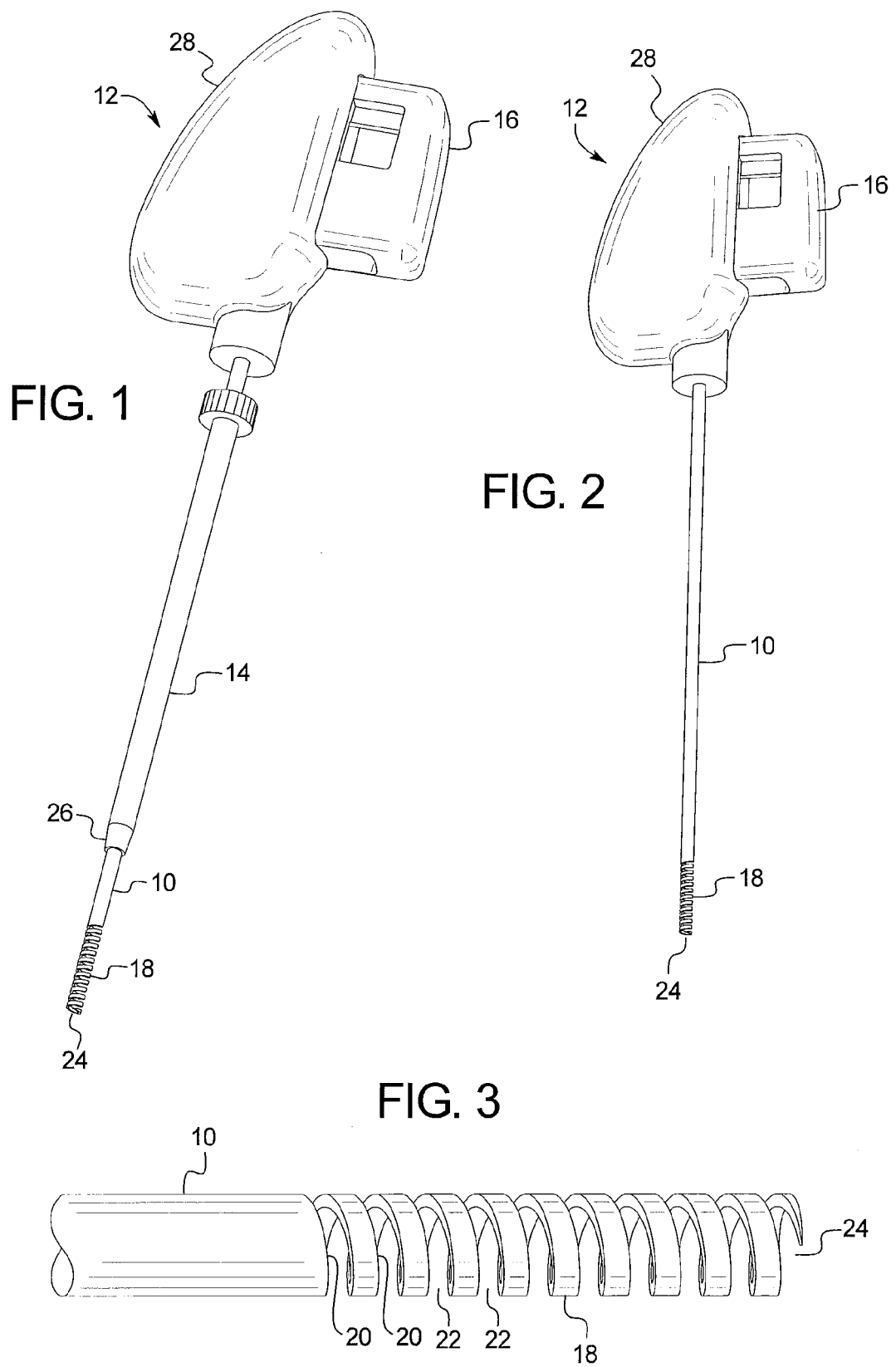

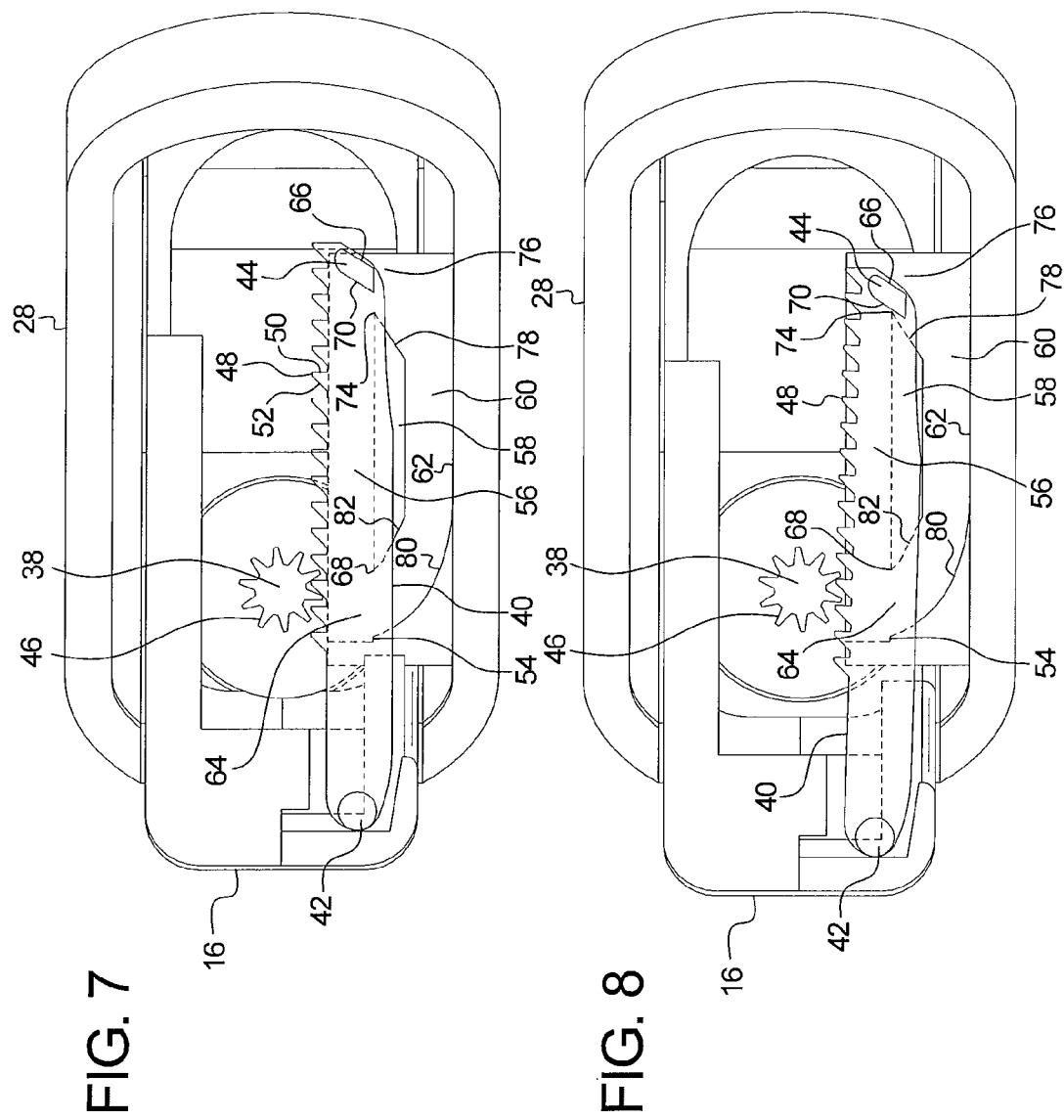

ROTATIONAL DRIVE SYSTEM FOR A BIOPSY MEMBER

This application claims priority to U.S. Provisional Application No. 61/675,438, filed Jul. 25, 2012, which is hereby incorporated by reference herein.

BACKGROUND

The present invention relates generally to medical devices and more particularly to a biopsy member.

It is often necessary to obtain tissue samples for medical analysis and diagnosis. Physicians in many specialties commonly obtain biopsy samples in order to detect abnormalities, such as cancer.

Although there are numerous biopsy systems available, many biopsy systems use a member to cut a sample from inside a patient's body. Typically, the member may be a needle with a hollow longitudinal lumen and a sharp edge for cutting tissue. In order to retrieve the biopsy sample, the needle is inserted through the patient's skin, and the sharp edge cuts a tissue sample from inside the patient's body. The tissue sample is then collected inside of the longitudinal lumen of the needle. Alternatively, the biopsy member could be a brush or other collection instrument.

Various types of stylets, cannulas, and other tissue collection structures may also be used in conjunction with a biopsy member. For example, a stylet with a pointed tip may be inserted through the member, and may be used to guide the biopsy member to the desired target tissue. The member may also be inserted through a guide cannula or cutting cannula. The cannula may provide a pathway through non-targeted tissue to minimize damage to the non-targeted tissue. If the cannula has a sharp distal edge for cutting, the cannula may also be used to cut the tissue sample from the target tissue.

After the biopsy sample has been cut from the target tissue, the biopsy member may be withdrawn from the patient, and the biopsy sample may be retrieved from the distal end of the member. Alternatively, the biopsy sample may be retrieved from the longitudinal lumen of a biopsy needle while the needle remains in the patient's body by drawing the biopsy sample proximally through the lumen and out an exterior port of the biopsy needle.

One type of biopsy member that is used to collect biopsy samples has a helical screw blade at the distal end of a needle. This type of biopsy member is typically driven into the target tissue by rotating the member so that the helical blade screws into the target tissue like a corkscrew. The tissue sample may then be separated from the target tissue by advancing a cutting cannula over the helical screw blade, or by withdrawing the member which causes the helical blade to longitudinally cut through portions of the sample that extend through the helical gap of the blade.

Biopsy members with helical screw blades are typically driven into the tissue by manually rotating the member. However, this has some disadvantages in practice. In particular, the length of time that a medical procedure takes increases the cost of the procedure and also can increase the anxiety of a patient. However, compared to some spring-loaded biopsy systems, manually driven helical screw members can be slower to use. Manually rotating a helical screw member can also be tedious for a physician, especially for a physician who performs numerous biopsies. In addition, patients may be more psychologically affected by a manual biopsy system, when the patient is able to view the physician repeatedly moving his hand and/or wrist as the member is driven into their body. By comparison, a patient may be psychologically more comfortable with a biopsy system where the physician's body movements are minimized during the driving step of the procedure.

Accordingly, the inventor believes that an improved drive system for a biopsy member would be desirable for collecting biopsy samples.

SUMMARY

A drive system is described for rotatably driving a biopsy member in a single direction. The drive system has a rack that rotates into engagement with a pinion during a drive stroke and rotates out of engagement with the pinion during a return stroke. The rack is rotated by a guide member that follows a first trackway during the drive stroke and a second trackway during the return stroke. The pinion is connected to the biopsy member and is driven by the rack during the drive stroke but is not driven during the return stroke. The inventions herein may also include any other aspect described below in the written description, the claims, or in the attached drawings and any combination thereof.

BRIEF DESCRIPTION OF SEVERAL VIEWS OF THE DRAWINGS

The invention may be more fully understood by reading the following description in conjunction with the drawings, in which:

FIG. 1 is a perspective view of a biopsy system including a cutting cannula;

FIG. 2 is a perspective view of the biopsy system without the cutting cannula;

FIG. 3 is a close-up view of the distal end of the biopsy member;

FIG. 7 is a top view of the internal mechanism of the handle, showing the rack near the end of the drive stroke and the beginning of the return stroke;

FIG. 8 is a top view of the internal mechanism of the handle, showing the rack near the beginning of the return stroke.

DETAILED DESCRIPTION

Figure 4:
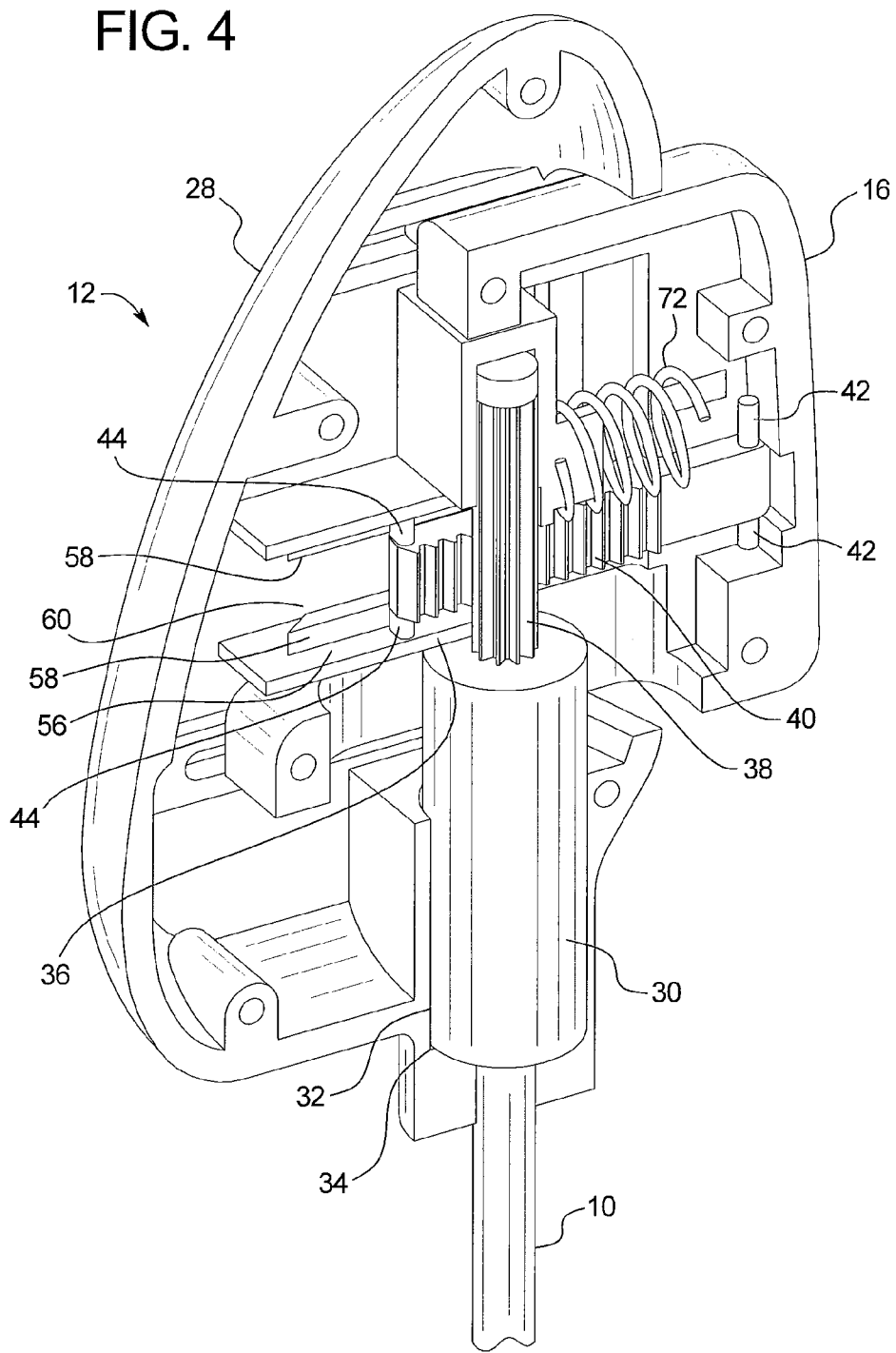
FIG. 4 is a perspective view of the internal mechanism of the handle.

Referring now to the figures, and particularly to FIGS. 1-3, a biopsy member 10 and a drive system 12 for the member 10 are shown. As shown in FIG. 1, the biopsy member 10 may be inserted through a cutting cannula 14 to reach a target tissue. Typically, a stylet with a pointed tip will usually be initially inserted through the cannula 14 so that the pointed tip is exposed at the distal end of the cannula 14. The stylet and cannula 14 may then be driven into a patient's body by manually pushing the stylet and cannula 14 together through the patient's tissues. Once the distal ends of the stylet and cannula 14 are located close to the target tissue, the stylet may be withdrawn from the cannula 14. The biopsy member 10 may then be inserted through the cannula 14 and may be longitudinally slid through the cannula 14 until the distal end of the member 10 reaches the distal end of the cannula 14.

The trigger 16 is then repeatedly pressed and released to rotationally drive the biopsy member 10 into the target tissue. The rotational movement of the biopsy member 10 causes the hollow helical screw blade 18 at the distal end of the member 10 to screw into the target tissue, which pulls the member 10 into the target tissue. Once the desired tissue sample is positioned within the lumen 20 of the member 10, the tissue sample can be separated from the target tissue by advancing the cannula 14 distally over the helical screw blade 18 or by withdrawing the member 10 into the cannula 14. In either case, the tissue sample within the lumen 20 of the member 10 will initially be connected to the target tissue through the helical gap 22 of the screw blade 18 and at the distal opening 24 of the member 10. By advancing the cannula 14 over the screw blade 18, the sharp distal edge 26 of the cannula 14 cuts through the connecting tissues extending through the helical gap 22 of the member 10. Alternatively, if the member 10 is withdrawn into the cannula 14, the proximal edge of the helical screw 18 cuts through the connecting tissues extending through the helical gap 22. In either event, the connected tissue at the distal opening 24 of the member 10 typically does not need to be separately cut loose from the target tissue, since this portion of the tissue will usually tear away when the biopsy member 10 is withdrawn. Thus, the tissue sample that is retrieved after the procedure is complete is a cylindrical core disposed in the distal end of the lumen 20 of the member 10.

As shown in FIGS. 2 and 4, a drive system 12 may be provided with the biopsy member 10 to rotationally drive the biopsy member 10 without having to manually rotate the member 10. Although the drive system 12 may be used with other types of biopsy members, the drive system 12 may be particularly useful with biopsy needles 10 that have a hollow helical screw blade 18 at the distal end of the needle 10. Thus, as shown in FIG. 4, the member 10 is longitudinally fixed to the housing 28 of the drive system 12 and is rotatable relative to the housing 28. This may be accomplished, for example, by affixing the proximal end of the member 10 to a collar 30 that is rotatable within a bore 32 in the housing 28 and abuts a lower stop 34 and an upper stop 36. A pinion 38 is also affixed to the collar 30 so that the pinion 38 is rotationally fixed to the member 10 and is rotatable within the housing 28. Although components may be rotationally or otherwise fixed together herein by bonding separate components together, components that are fixed together and provide more than one function may also be made as integral components.

Figure 5:
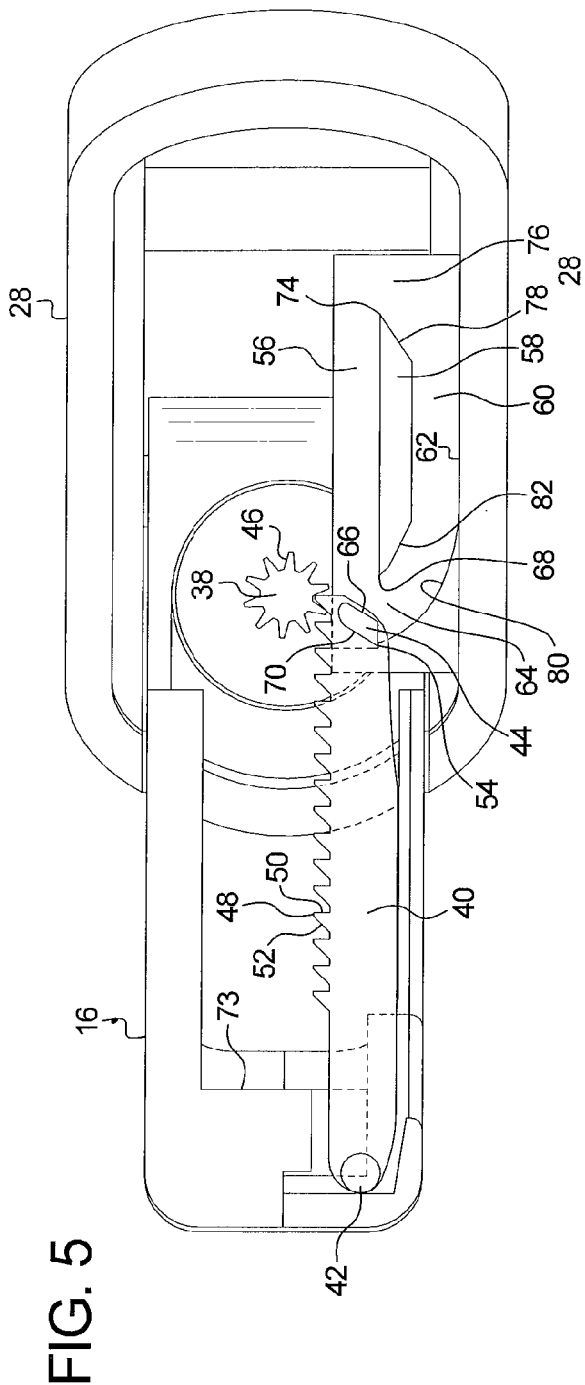
FIG. 5 is a top view of the internal mechanism of the handle, showing the rack at the end of the return stroke.

As shown in FIGS. 5-9, a rack 40 rotates the pinion 38 during a drive stroke when the trigger 16 is pushed, but does not rotate the pinion 38 during the return stroke when the trigger 16 returns to its initial position. Preferably, the trigger 16 is biased by a spring 72 toward its initial position so that the spring 72 pushes the trigger 16 back to its initial position during the return stroke when the physician releases the trigger 16 at the end of the drive stroke. Although various spring arrangements are possible, the spring 72 may be biased between the housing 28 and the trigger 16 as shown in FIG. 4. Although not shown in FIG. 4 since FIG. 4 only shows half of the trigger 16, the other half of the trigger 16 may provide an abutting surface 73 for the spring 72 as shown in FIG. 5. Because the drive system 12 only rotates the pinion 38 and the member 10 during the drive stroke, the member 10 rotates in a single direction, which is the direction that drives the helical screw blade 18 into the targeted tissue.

The rack 40 may be pivotally connected to the trigger 16 around a pin 42. Preferably, as shown in FIG. 4, the rack 40 has two pins 42 on opposite sides of the rack 40 that pivotally connect the rack 40 to the trigger 16. At the opposite end of the rack 40, the rack 40 may be provided with a guide member 44. The rack 40 may also be provided with two guide members 44 on opposite sides of the rack 40 as shown in FIG. 4.

The pinion 38 and the rack 40 each have a series of teeth 46, 48 that are complementary to each other to allow the rack 40 to drive the pinion 38. In the case of the pinion 38, the teeth 46 are positioned circumferentially around the pinion 38, and the teeth 48 of the rack 40 are positioned in a generally longitudinal orientation. Preferably, the teeth 48 of the rack 40 are asymmetrical so that the first tooth surfaces 50 facing in the direction of the drive stroke are shaped differently than the second tooth surfaces 52 facing in the direction of the return stroke. For example, the first tooth surfaces 50 are preferably substantially vertical or acute. By contrast, the second tooth surfaces 52 are preferably obtuse. Thus, as described below, the first tooth surfaces 50 have a tendency to remain engaged with the pinion teeth 46, and the second tooth surfaces 52 have a tendency to disengage from the pinion teeth 46.

As shown in FIG. 5, the guide member 44 is initially positioned within a notch 54 when the trigger 16 is in its initial position. The notch 54 is positioned to engage the rack teeth 48 with the pinion teeth 38. The notch 54 is also aligned with a first trackway 56 positioned between a divider 58 and the pinion 38. The divider 58 also defines a second trackway 60 on the opposite side of the divider 58 between a wall 62 of the housing 28 and the divider 58. As shown in FIG. 4, the housing 28 may have two first and second trackways 56, 60 and dividers 58 on opposite sides of the rack 40.

When the trigger 16 is pushed, the rack 40 moves longitudinally relative to the pinion 38 along the drive stroke. As the rack 40 begins the drive stroke, the guide member 44 passes by the second opening 64 of the second trackway 60. However, the guide member 44 tends to remain along the path of the first trackway 56 for several reasons. As noted above, the shape of the first tooth surfaces 50 of the rack 40 make the teeth 46, 48 of the pinion 38 and rack 40 less inclined to separate when the rack 40 moves in the direction of the drive stroke than when the rack 40 moves in the direction of the return stroke. Also, the biopsy member 10 and drive system 12 will typically be used in a generally vertical orientation so gravity will have a minimal influence on lateral movement of the rack 40. Further, the guide member 44 may be shaped and sized to encourage the guide member 44 to remain in the first trackway 56 instead of passing into the second trackway 60 through the second opening 64. That is, the guide member 44 may be provided with a first guide surface 66 facing in the direction of the drive stroke which may be shaped acutely. As a result, when the first guide surface 66 contacts the first edge 68 of the divider 58, the first guide surface 66 forces the guide member 44 into the first trackway 56. The overall width of the guide member 44 may also be sized to limit the opportunity for the guide member 44 to pass through the second opening 64 of the second trackway 60. Thus, the overall width of the guide member 44 between the leading edge of the first guide surface 66 and the trailing edge of the second guide surface 70 may be minimally smaller than the width of the second opening 64 of the second trackway 60. As a result, the guide member 44 only needs to travel a very short distance (i.e., the clearance length between the second opening 64 and the overall width of the guide member 44) before the first guide surface 66 potentially contacts the first edge 68 of the divider 58. Once the guide member 44 reaches the point of potential contact between the first guide surface 66 and the first edge 68 of the divider 58, the guide member 44 will be prevented from passing into the second opening 64 of the second trackway 60 by the first guide surface 66 and the first edge 68 of the divider 58.

Figure 6:
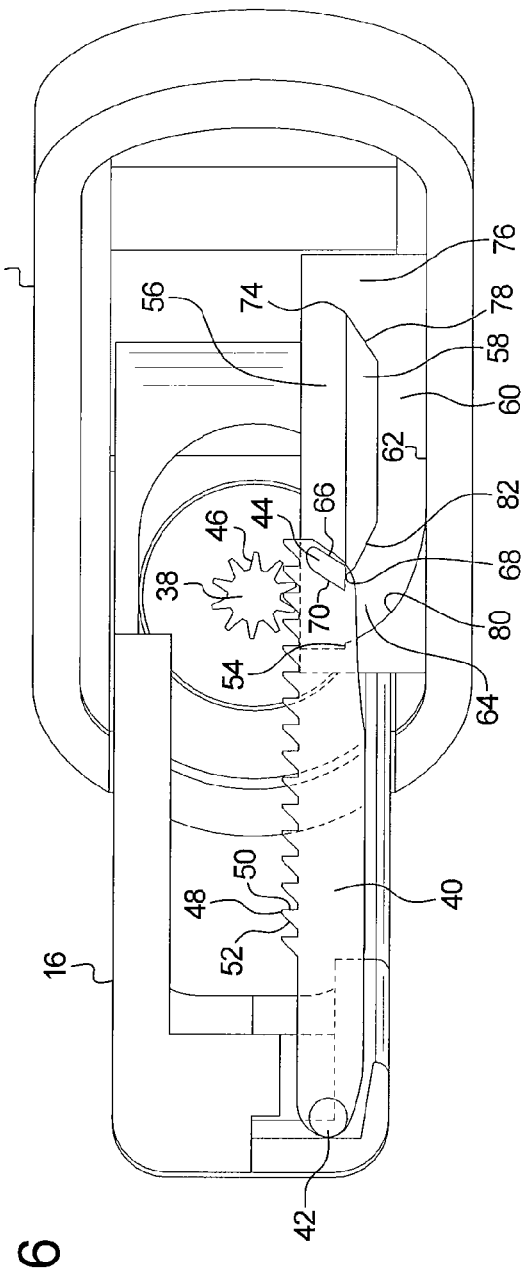
FIG. 6 is a top view of the internal mechanism of the handle, showing the rack near the beginning of the drive stroke.

As shown in FIG. 6, once the guide member 44 passes by the second opening 64 of the second trackway 60, the guide member 44 continues along the first trackway 56 during the drive stroke. As the physician continues to push the trigger 16, the spring 72 is compressed, and the rack 40 continues along the drive stroke. As the rack 40 moves along the drive stroke, the rack teeth 48 rotate the pinion teeth 46, which correspondingly rotates the biopsy member 10.

As shown in FIG. 7, when the rack 40 reaches the end of the drive stroke, the guide member 44 passes the second edge 74 of the divider 58 and is located near the first opening 76 of the second trackway 60. At this point, the physician releases the trigger 16, and the spring 72 forces the trigger 16 to return to its initial position. The rack 40 is then pulled by the trigger 16 in the reverse direction, which begins the return stroke. However, because the second tooth surfaces 52 of the rack teeth 48 may be obtuse, at least on the rack teeth 48 that are engaged with the pinion 38 at the end of the drive stroke and the beginning of the return stroke, the rack 40 is pushed away from the pinion 38 instead of rotating the pinion 38 in the reverse direction. While the rack teeth 48 could theoretically rotate the pinion 38 in reverse even with obtuse second tooth surfaces 52, normal friction between the biopsy member 10 and the targeted tissue and between the collar 30 and the bore 32, and elsewhere in the system, typically will provide sufficient initial resistance for the pinion 38 to force the rack teeth 48 away from the pinion teeth 46.

As shown in FIG. 8, as the rack moves in the reverse direction with the trigger 16, the rack pivots about the pins 42 and the guide member 44 moves into the first opening 76 of the second trackway 60. The second guide surface 70 of the guide member 44 and the first divider surface 78 are preferably shaped to encourage the guide member 44 to move through the first opening 76 into the second trackway 60. That is, the second guide surface 70 facing in the direction of the return stroke may be shaped obtusely. Also, the first divider surface 78 located near the beginning of the return stroke, and the end of the drive stroke, and connecting the first and second trackways 56, 60 may be sloped away from the first trackway 56 in the direction of the return stroke. As a result, when the second guide surface 70 of the guide member 44 contacts the first divider surface 78, the guide member 44 is forced into the second trackway 60. This further rotates the rack 40 until the rack teeth 48 eventually disengage from the pinion teeth 46 as the guide member 44 moves into the second trackway 60. Because of the obtuse shape of the second guide surface 70, only a small separating bias between the rack and pinion teeth 48, 46 is needed to force the guide member 44 into the second trackway 60. This is because once the trailing edge (i.e., the bottom edge in the figures) of the second guide surface 70 moves past the second edge 74 of the divider 58, the obtusely shaped second guide surface 70 slides along the second edge 74 of the divider 58 to force the guide member 44 all the way into the second trackway 60.

Figure 9:
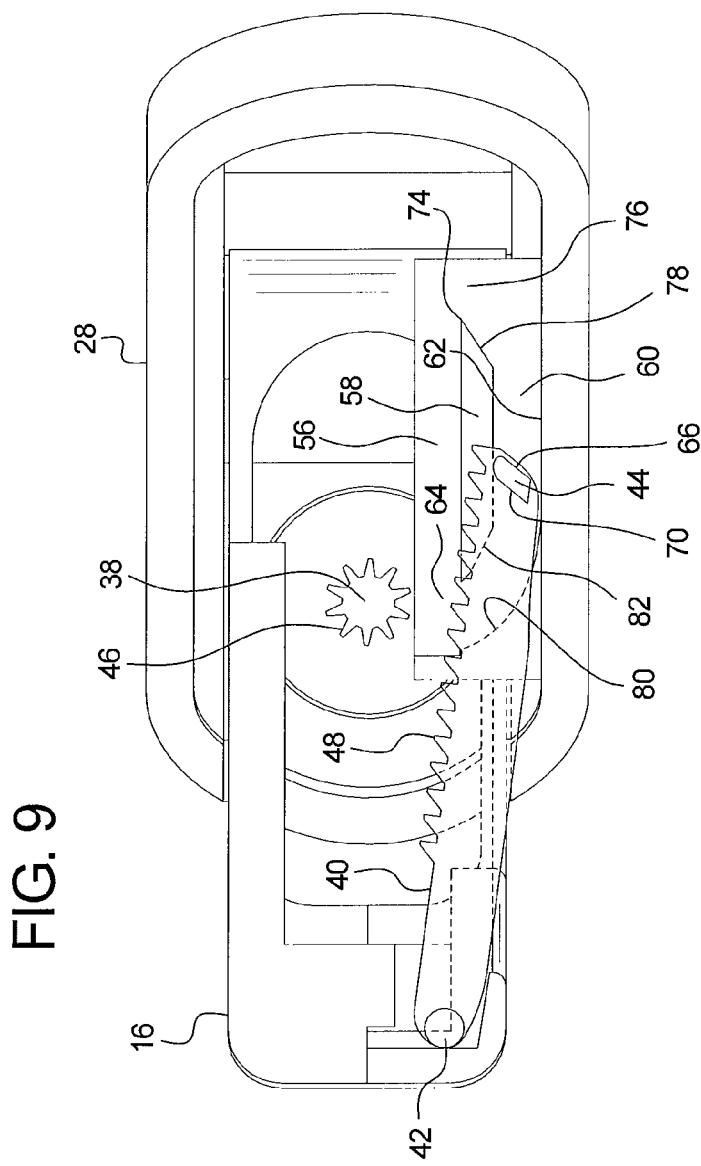
FIG. 9 is a top view of the internal mechanism of the handle, showing the rack in the middle of the return stroke.

As shown in FIG. 9, once the guide member 44 passes into the second trackway 60, the guide member 44 continues along the second trackway 60 during the return stroke. As the rack 40 moves along the return stroke, the pinion teeth 46 and the rack teeth 48 are separated. Thus, the pinion 38 and the biopsy member 10 do not rotate during the return stroke.

As the guide member 44 nears the end of the return stroke, the guide member 44 follows a trackway surface 80 that is sloped along the return direction toward the first trackway 56. This forces the guide member 44 through the second opening 64 of the second trackway 60 and into the first trackway 56. The second divider surface 82 located near the end of the return stroke and connecting the first and second trackways 56, 60 may be sloped away from the first trackway 56 in the direction of the drive stroke. This provides the guide member 44 with the necessary clearance for the guide member 44 to follow the sloped trackway surface 80 back to the first trackway 56. Also, the sloped second divider surface 82 forms a pointed first edge 68 and the intersection of the second opening 64 and the first trackway 56. Likewise, the sloped first divider surface 78 forms a pointed second edge 74 at the intersection of the first opening 76 and the first trackway 56.

Once the guide member 44 passes through the second opening 64, the spring 72 continues to force the trigger 16 and rack 40 to move in the return direction. As a result, the guide member 44 is pulled back into the notch 54 as the trigger 16 returns to its initial position. Although it is possible that the rack 40 could also be influenced by a spring to move between the first and second trackways 56, 60, the drive system 12 may function without any spring biasing the rack 40 around the pivot pins 42. Thus, as described, the guide member 44 may follow the first and second trackways 56, 60 due solely to the geometry of the teeth 46, 48, guide member 44, divider 58, and first and second trackways 56, 60.

An advantage of the drive system 12 is that a biopsy member 10 may be rotated in a single direction by actuating the trigger 16 back-and-forth along a drive stroke and a return stroke. As described, the rack 40 engages and rotates the pinion 38 during the drive stroke, but is separated from and does not rotate the pinion 38 during the return stroke. This is accomplished by first and second trackways 56, 60 that rotate the rack 40 into engagement during the drive stroke and rotate the rack 40 out of engagement during the return stroke. This may make driving the helical screw blade 18 biopsy member 10 easier for physicians and less traumatic for patients.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

I claim:

1. A drive system for rotationally driving a biopsy member, comprising: a housing comprising a first trackway and a second trackway and a divider between said first and second trackways; a pinion comprising a series of first teeth disposed circumferentially on the pinion, said pinion being connected to said housing and being rotatable relative to said housing and being configured to be rotationally fixed to said biopsy member; a trigger connected to said housing and being moveable relative to said housing during a drive stroke and a return stroke; a rack comprising a series of second teeth disposed longitudinally on the rack, said rack being connected to said housing and being pivotal relative to said housing and moving in a first direction during said drive stoke and moving in a second direction during said return stroke, said rack comprising a guide member following said first and second trackways; wherein said guide member follows said first trackway during said drive stroke, said guide member and said first trackway engaging said first and second teeth of said pinion and said rack as said rack moves in said first direction, said rack thereby rotating said pinion during said drive stroke, and said guide member follows said second trackway during said return stroke, said guide member and said second trackway separating said first and second teeth of said pinion and said rack as said rack moves in said second direction, said rack thereby not rotating said pinion during said return stroke.

2. The drive system according to claim 1, wherein each of said second teeth of said rack comprises a first tooth surface facing in said first direction and a second tooth surface facing in said second direction, said first tooth surface being substantially vertical or acute.

3. The drive system according to claim 1, wherein each of said second teeth of said rack comprises a first tooth surface facing in said first direction and a second tooth surface facing in said second direction, at least one of said second tooth surfaces in engagement with said first teeth near an end of said drive stroke being obtuse.

4. The drive system according to claim 1, wherein said guide member comprises a first guide surface facing in said first direction and a second guide surface facing in said second direction, said first guide surface being acute, said first guide surface thereby forcing said guide member into said first trackway near a beginning of said drive stroke upon contact between said first guide surface and said divider.

5. The drive system according to claim 1, wherein said guide member comprises a first guide surface facing in said first direction and a second guide surface facing in said second direction, said second guide surface being obtuse, said second guide surface thereby forcing said guide member into said second trackway near a beginning of said return stroke upon contact between said second guide surface and said divider.

6. The drive system according to claim 1, wherein said divider comprises a first divider surface connecting said first and second trackways near an end of said drive stroke, said first divider surface sloping along said second direction away from said first trackway, said first divider surface thereby forcing said guide member into said second trackway near a beginning of said return stroke upon contact between said first divider surface and said guide member.

7. The drive system according to claim 1, wherein said divider comprises a second divider surface connecting said first and second trackways near an end of said return stroke, said second divider surface sloping along said first direction away from said first trackway, said second divider surface thereby providing clearance for said guide member to move into said first trackway near said end of said return stroke upon contact between said second divider surface and said guide member.

8. The drive system according to claim 1, wherein said second trackway comprises a trackway surface near an end of said return stroke, said trackway surface sloping along said second direction toward said first trackway, said trackway surface thereby forcing said guide member into said first trackway near said end of said return stroke.

9. The drive system according to claim 8, further comprising a notch at an end of said trackway surface and at said end of said return stroke, said notch being aligned with said first trackway.

10. The drive system according to claim 1, wherein said rack is pivotally connected to said trigger.

11. The drive system according to claim 1, further comprising a spring biasing said trigger, said spring being stressed during said drive stroke and forcing said trigger to move along said return stroke.

12. The drive system according to claim 1, wherein said rack is not biased by any spring around said pivotal connection toward said first trackway or said second trackway.

13. The drive system according to claim 1, wherein said biopsy member is longitudinally fixed to said housing, said biopsy member comprising a hollow helical screw blade at a distal end of said biopsy member.

14. The drive system according to claim 1, wherein said rack is pivotally connected to said trigger, further comprising a spring biasing said trigger, said spring being stressed during said drive stroke and forcing said trigger to move along said return stroke, and wherein said biopsy member is longitudinally fixed to said housing, said biopsy member comprising a hollow helical screw blade at a distal end of said biopsy member.

15. The drive system according to claim 14, wherein each of said second teeth of said rack comprises a first tooth surface facing in said first direction and a second tooth surface facing in said second direction, said first tooth surface being substantially vertical or acute, and at least one of said second tooth surfaces in engagement with said first teeth near an end of said drive stroke being obtuse.

16. The drive system according to claim 15, wherein said guide member comprises a first guide surface facing in said first direction and a second guide surface facing in said second direction, said first guide surface being acute, said first guide surface thereby forcing said guide member into said first trackway near a beginning of said drive stroke upon contact between said first guide surface and said divider, and said second guide surface being obtuse, said second guide surface thereby forcing said guide member into said second trackway near a beginning of said return stroke upon contact between said second guide surface and said divider.

17. The drive system according to claim 16, wherein said divider comprises a first divider surface connecting said first and second trackways near an end of said drive stroke, said first divider surface sloping along said second direction away from said first trackway, said first divider surface thereby forcing said guide member into said second trackway near a beginning of said return stroke upon contact between said first divider surface and said guide member, said divider comprises a second divider surface connecting said first and second trackways near an end of said return stroke, said second divider surface sloping along said first direction away from said first trackway, said second divider surface thereby providing clearance for said guide member to move into said first trackway near said end of said return stroke upon contact between said second divider surface and said guide member, and said second trackway comprises a trackway surface near said end of said return stroke, said trackway surface sloping along said second direction toward said first trackway, said trackway surface thereby forcing said guide member into said first trackway near said end of said return stroke.

18. The drive system according to claim 17, wherein said rack is not biased by any spring around said pivotal connection toward said first trackway or said second trackway.

19. The drive system according to claim 1, wherein said rack is not biased by any spring around said pivotal connection toward said first trackway or said second trackway, said guide member comprises a first guide surface facing in said first direction and a second guide surface facing in said second direction, said first guide surface being acute, said first guide surface thereby forcing said guide member into said first trackway near a beginning of said drive stroke upon contact between said first guide surface and said divider, and said second guide surface being obtuse, said second guide surface thereby forcing said guide member into said second trackway near a beginning of said return stroke upon contact between said second guide surface and said divider.

20. The drive system according to claim 19, wherein said divider comprises a first divider surface connecting said first and second trackways near an end of said drive stroke, said first divider surface sloping along said second direction away from said first trackway, said first divider surface thereby forcing said guide member into said second trackway near said beginning of said return stroke upon contact between said first divider surface and said guide member, and said second trackway comprises a trackway surface near an end of said return stroke, said trackway surface sloping along said second direction toward said first trackway, said trackway surface thereby forcing said guide member into said first trackway near said end of said return stroke.

* * * * *